(12) United States Patent
Jung

(10) Patent No.: US 10,663,730 B2
(45) Date of Patent: May 26, 2020

(54) HEAD MOUNTED DISPLAY DEVICE

(71) Applicant: LG ELECTRONICS INC., Seoul (KR)

(72) Inventor: Jaeduck Jung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 156 days.

(21) Appl. No.: 15/790,869

(22) Filed: Oct. 23, 2017

(65) Prior Publication Data

US 2018/0113312 A1    Apr. 26, 2018

(30) Foreign Application Priority Data

Oct. 24, 2016 (KR) ........................ 10-2016-0138499

(51) Int. Cl.
| | | |
|---|---|---|
| *G02B 27/01* | (2006.01) | |
| *A61H 7/00* | (2006.01) | |
| *G16H 20/30* | (2018.01) | |
| *G16H 30/20* | (2018.01) | |
| *G16H 40/67* | (2018.01) | |
| *G16H 40/63* | (2018.01) | |

(52) U.S. Cl.
CPC .......... *G02B 27/0172* (2013.01); *A61H 7/00* (2013.01); *A61H 7/001* (2013.01); *G16H 20/30* (2018.01); *G16H 30/20* (2018.01); *G16H 40/63* (2018.01); *G16H 40/67* (2018.01); *A61H 2201/0149* (2013.01); *A61H 2201/0207* (2013.01); *A61H 2201/0214* (2013.01); *A61H 2201/1645* (2013.01); *A61H 2201/5043* (2013.01); *A61H 2201/5046* (2013.01); *A61H 2201/5048* (2013.01); *A61H 2201/5058* (2013.01); *A61H 2201/5061* (2013.01); *A61H 2201/5082* (2013.01); *A61H 2201/5089* (2013.01); *A61H 2201/5092* (2013.01); *A61H 2203/0431* (2013.01); *A61H 2230/625* (2013.01); *G02B 2027/0141* (2013.01)

(58) Field of Classification Search
CPC ........ G02B 27/0172; G02B 2027/0141; G16H 20/30; G16H 30/20; G16H 40/67; G16H 40/63; A61H 7/00; A61H 7/001; A61H 7/0149; A61H 7/0207; A61H 7/0214; A61H 7/1645; A61H 7/5043; A61H 7/5046; A61H 7/5048; A61H 7/5058; A61H 7/5061; A61H 7/5082; A61H 7/5089; A61H 7/5092; A61H 2203/0431; A61H 2230/625
See application file for complete search history.

(56) References Cited

U.S. PATENT DOCUMENTS

2011/0055720 A1* 3/2011 Potter ..................... G06F 3/017
                                                                    715/747
2018/0075764 A1* 3/2018 Bachani ................ G16H 50/30

\* cited by examiner

*Primary Examiner* — Wing H Chow
(74) *Attorney, Agent, or Firm* — Birch, Stewart, Kolasch & Birch, LLP

(57) ABSTRACT

A head mounted display (HMD) device including a display configured to display an image; a communication processor configured to communicate with a massage chair for performing a massage; and a controller configured to receive massage information from the massage chair about the massage, and display an image on the display corresponding to the massage based on the received massage information.

10 Claims, 10 Drawing Sheets

HEAD MOUNTED DISPLAY DEVICE

CROSS-REFERENCE TO RELATED APPLICATIONS

This application claims priority to Korean Patent Application No. 10-2016-0138499 filed in the republic of Korea on Oct. 24, 2016, the entire contents of which is hereby incorporated by reference in its entirety.

BACKGROUND

Field

The present disclosure relates to a head mounted display (HMD) device which is capable of communicating with a massage chair to display a massage part or a massage status.

Discussion of the Related Art

Recently, fitness equipment (e.g., running machine) or massage apparatuses have been developed for maintaining or enhancing health and fitness in home or health clubs or relieving fatigue and stress and are widely used in real life. In particular, since a demand for loosening knotted muscles or relieving fatigue and stress through massage increases, interest in massage apparatuses is increasing. A massage is one of the medical therapies that help blood circulation and relieve fatigue by sweeping, nipping, pressing, pulling, tapping, or moving with a hand or a special instrument. In addition, a massage apparatus performs a massage by a mechanical device. A representative example of the massage apparatus is a massage chair that allows a user to sit comfortably and receive a massage.

Massage chairs are becoming more and more diverse in function, and thus, input devices for controlling various functions of the massage chairs are installed in the massage chairs. This is disclosed in Korean Patent Application Publication No. 10-2011-0124620.

Since receiving a massage using a massage chair generally takes a long time, a head mounted display (HMD) device can be utilized as a device capable of relieving a user's boredom.

SUMMARY

A first object of the present disclosure is to provide a head mounted display (HMD) device which displays an image in which a massage part is massaged based on massage information, so as to provide a realistic experience to a user who receives a massage.

A second object of the present disclosure is to display a user's health condition or a muscle's relaxed state which is changed according to a massage is progressed, so as to provide a massage progress status to a user who receives a massage.

According to an aspect for achieving the first object of the present disclosure, an HMD device can receive massage information from a massage chair and display an image in which a massage part is massaged, based on the received massage information.

According to an aspect for achieving the second object of the present disclosure, an HMD device may display a body image showing a user's health condition based on user's health information and display a user's health condition changed as a massage is progressed. Additionally, the HMD device may display an image showing that a muscle is relaxed.

According to a first aspect of the present disclosure, a user can relieve boredom and experience a realistic massage by displaying an image in which a massage part is massaged.

According to a second aspect of the present disclosure, it is possible to provide an environment that allows a user to easily confirm a use's health condition or a massage progress status by displaying a user's health condition or a degree of relax of muscles.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by illustration only, and thus are not limitative of the present invention, and wherein.

DETAILED DESCRIPTION OF THE EMBODIMENTS

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

A head mounted display (HMD) used herein may include, for example, a wearable device (e.g., smart glass) and the like. However, except for the configurations applicable only to the HMD the configurations according to the embodiments described herein may also be applied to mobile terminals, such as smart phones, laptop computers, digital broadcasting terminals, personal digital assistants (PDAs), portable multimedia players (PMPs), navigations, slate PCs, tablet PCs, ultrabooks, and smartwatch.

Figure 1:
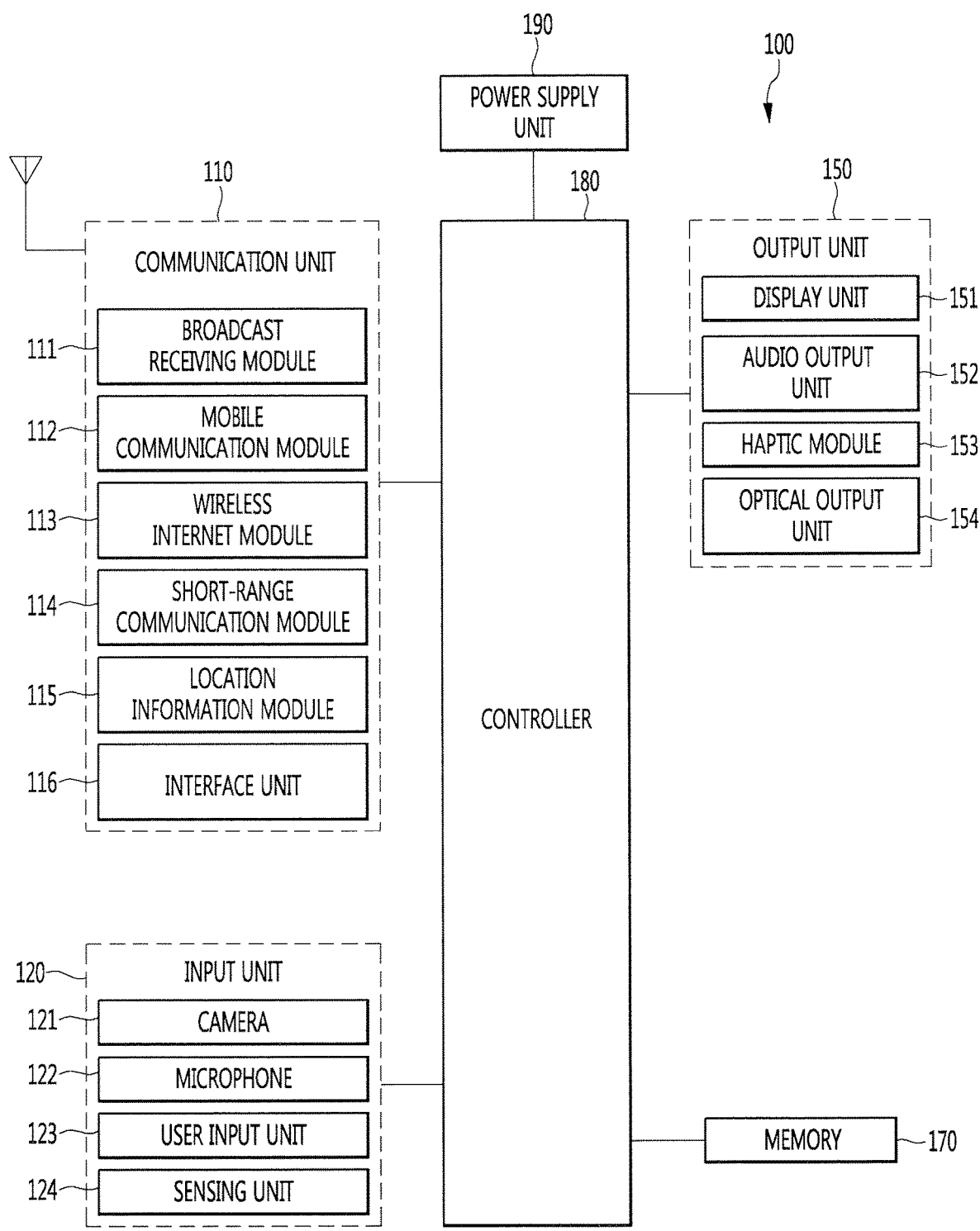
FIG. 1 is a block diagram illustrating a head mounted display (HMD) related to the present disclosure.

FIG. 1 is a block diagram illustrating an HMD related to the present disclosure. The HMD 100 can include a communication unit 110, an input unit 120, an output unit 150, a memory 170, a controller 180, and a power supply unit 190. The components shown in FIG. 1 are not necessarily essential for implementing the HMD, and the HMD described herein may include more or fewer components than those listed above.

More specifically, the communication unit 110 among the above components may include at least one module enabling wireless communication between the HMD 100 and a wireless communication system, between the HMD 100 and another HMD 100, between the HMD 100 and a mobile or stationary terminal, between the HMD 100 and a controller, between the HMD 100 and a camera installed in the outside and capable of wireless communication, between the HMD 100 and a massage chair, or between the HMD 100 and an external server. Additionally, the communication unit 110 may include at least one module which connects the HMD 100 to at least one network.

The communication unit 110 may include at least one of a broadcast receiving module 111, a mobile communication module 112, a wireless Internet module 113, a short-range communication module 114, a location information module 115, and an interface unit 116.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof. Additionally, the input unit 120 may include a sensing unit 124.

The output unit 150 is typically configured to output various types of information, such as audio, video, tactile output, and the like. The output unit 150 is shown having a display unit 151, an audio output unit 152, a haptic module 153, and an optical output unit 154. The memory 170 is typically implemented to store data to support various functions or features of the HMD 100. For instance, the memory 170 may be configured to store application programs executed in the HMD 100, data or instructions for operations of the HMD 100, and the like. Some of these application programs may be downloaded from an external server via wireless communication.

Other application programs may be installed within the HMD 100 at time of manufacturing or shipping, which is typically the case for basic functions of HMD 100 (for example, receiving a call, placing a call, receiving a message, sending a message, and the like). It is common for application programs to be stored in the memory 170, installed in the HMD 100, and executed by the controller 180 to perform an operation (or function) for the HMD 100. The controller 180 typically functions to control overall operation of the HMD 100, in addition to the operations associated with the application programs. The controller 180 can provide or process information or functions appropriate for a user by processing signals, data, information and the like, which are input or output by the various components depicted in FIG. 1, or activating application programs stored in the memory 170.

As one example, the controller 180 controls some or all of the components illustrated in FIG. 1 according to the execution of an application program that have been stored in the memory 170. The power supply unit 190 can be configured to receive external power or provide internal power in order to supply appropriate power required for operating elements and components included in the HMD 100. The power supply unit 190 may include a battery, and the battery may be configured to be embedded in the HMD, or configured to be detachable from the HMD.

At least some of the components may cooperate with each other so as to implement the operation, control, or control method of the HMD according to various embodiments described below. Additionally, the operation, control, or control method of the HMD may be implemented on the HMD by the execution of at least one application program stored in the memory 170.

Referring still to FIG. 1, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The broadcast managing entity may be a server which generates and transmits a broadcast signal and/or broadcast associated information, or a server which receives a pre-generated broadcast signal and/or broadcast associated information, and sends such items to the HMD. The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this instance, received by the mobile communication module 112.

The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external HMD, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the HMD 100. The wireless Internet module 113 can transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 can transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the wireless Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the HMD 100 and a wireless communication system, communications between the HMD 100 and another HMD 100, or communications between the HMD and a network where another HMD 100 (or an external server) is located, via wireless area networks. One example of the wireless area networks is a wireless personal area networks. Additionally, the short-range communication module 114 can transmit data to the massage chair and receive data from the massage chair.

Herein, the HMD 100 may be a device (e.g., a mobile phone, a smart phone, a smartwatch, a notebook computer, a controller, etc.) which is capable of exchanging data with the HMD 100. The short-range communication module 114 may detect (or recognize) a device capable of communicating with the HMD 100 around the HMD 100. Furthermore, when the detected device is a device authenticated to communicate with the HMD 100 according to the present disclosure, the controller 180 can transmit at least a part of data processed in the HMD 100 to the device through the short-range communication module 114, and may at least a part of data processed in the device to the HMD 100.

Accordingly, a user of the HMD 100 can use the data processed in the device through the HMD 100. For example, when the device receives a call, the user can make a phone call via the HMD 100, or when the device receives a message, the user can confirm the received message via the HMD 100.

The location information module 115 is generally configured to detect, calculate, derive or otherwise identify a position of the HMD 100. As an example, the location information module 115 includes a Global Position System (GPS) module, a Wi-Fi module, or both. If desired, the location information module 115 may alternatively or additionally function with any of the other modules of the wireless communication unit 110 to obtain data associated with the position of the HMD 100.

As one example, when the HMD 100 uses a GPS module, a position of the HMD 100 may be acquired using a signal sent from a GPS satellite. As another example, when the HMD 100 uses the Wi-Fi module, a position of the HMD 100 can be acquired based on information related to a wireless access point (AP) which transmits or receives a wireless signal to or from the Wi-Fi module.

The interface unit 116 serves as an interface with various types of external devices connected to the HMD 100. For example, the interface unit 116 may serve as an interface with a massage chair connected to the HMD 100. The interface unit 116 may include at least one of a wired/wireless headset port, an external charger port, a wired/wireless data port, a memory card port, a port for connecting a device equipped with an identification module, an audio I/O port, a video I/O port, and an earphone port. The HMD 100 can perform appropriate control associated with a connected external device in response to the connection of the external device to the interface unit 116.

The interface unit 160 serves as an interface for external devices to be connected with the HMD 100. For example, the interface unit 160 can receive data transmitted from an external device, receive power to transfer to elements and components within the HMD 100, or transmit internal data of the HMD 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like. Additionally, the interface unit 116 can transmit data to the massage chair or receive data from the massage chair.

The input unit 120 may be configured to permit various types of input to the HMD. Examples of such input include audio, image, video, data, and user input. Image and video input is often obtained using one or more cameras 121. Such cameras 121 can process image frames of still pictures or video obtained by image sensors in a video or image capture mode. The processed image frames can be displayed on the display unit 151 or stored in the memory 170. In some instances, the cameras 121 can be arranged in a matrix configuration to permit a plurality of images having various angles or focal points to be input to the HMD 100. As another example, the cameras 121 can be located in a stereoscopic arrangement to acquire left and right images for implementing a stereoscopic image.

The microphone 122 is generally implemented to permit audio input to the HMD 100. The audio input can be processed in various manners according to a function being executed in the HMD 100. If desired, the microphone 122 may include assorted noise removing algorithms to remove unwanted noise generated in the course of receiving the external audio.

The user input unit 123 is a component that permits input by a user. Such user input may enable the controller 180 to control operation of the HMD 100. The user input unit 123 may include one or more of a mechanical input element (for example, a key, a button located on a front and/or rear surface or a side surface of the HMD 100, a dome switch, a jog wheel, a jog switch, and the like), or a touch-sensitive input, among others. For example, a touch-type input unit may be at least one of a touch pad and a touch panel.

The sensing unit 124 is typically implemented using one or more sensors configured to sense internal information of the HMD 100, the surrounding environment of the HMD 100, user information, and the like. For example, in FIG. 1, the sensing unit 124 is shown having a proximity sensor and an illumination sensor.

If desired, the sensing unit 124 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The HMD 100 may be configured to utilize information obtained from sensing unit 124, and in particular, information obtained from one or more sensors of the sensing unit 124, and combinations thereof.

The sensing unit 124 is generally configured to sense one or more of internal information of the HMD, surrounding environment information of the HMD, user information, or the like. The controller 180 generally cooperates with the sensing unit 124 to control operation of the HMD 100 or execute data processing, a function or an operation associated with an application program installed in the HMD based on the sensing provided by the sensing unit 124. The sensing unit 124 may be implemented using any of a variety of sensors, some of which will now be described in more detail.

The proximity sensor may include a sensor to sense presence or absence of an object approaching a surface, or an object located near a surface, by using an electromagnetic field, infrared rays, or the like without a mechanical contact. The proximity sensor may be arranged at an inner region of the HMD covered by the touch screen, or near the touch screen.

The proximity sensor, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor can sense proximity of a pointer relative to the touch screen by changes of an electromagnetic field, which is responsive to an approach of an object with conductivity. In this instance, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor may sense proximity touch, and proximity touch patterns (for example, distance, direction, speed, time, position, moving status, and the like).

In general, the controller 180 processes data corresponding to proximity touches and proximity touch patterns sensed by the proximity sensor, and cause output of visual information on the touch screen. In addition, the controller 180 can control the HMD 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others. As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller can process the received signals, and then transmit corresponding data to the controller 180. Accordingly, the controller 180 can sense which region of the display unit 151 has been touched. Here, the touch controller may be a component separate from the controller 180, the controller 180, and combinations thereof.

In some embodiments, the controller 180 can execute the same or different controls according to a type of touch object that touches the touch screen or a touch key provided in addition to the touch screen. Whether to execute the same or different control according to the object which provides a touch input may be decided based on a current operating state of the HMD 100 or a currently executed application program, for example.

In addition, the touch sensor and the proximity sensor may be implemented independently, or in combination, to sense various types of touches. Such touches include a short (or tap) touch, a long touch, a multi touch, a drag touch, a flick touch, a pinch-in touch, a pinch-out touch, a swipe touch, a hovering touch, and the like. The touch sensor and the proximity sensor may be implemented individually, or in combination, to sense various types of touches. Such touches include a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor. Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the HMD 100. For example, the display unit 151 may display execution screen information of an application program executing at the HMD 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

In general, a 3D stereoscopic image may include a left image (e.g., a left eye image) and a right image (e.g., a right eye image). According to how left and right images are combined into a 3D stereoscopic image, a 3D stereoscopic imaging method can be divided into a top-down method in which left and right images are located up and down in a frame, an L-to-R (left-to-right or side by side) method in which left and right images are located left and right in a frame, a checker board method in which fragments of left and right images are located in a tile form, an interlaced method in which left and right images are alternately located by columns or rows, and a time sequential (or frame by frame) method in which left and right images are alternately displayed on a time basis.

Also, as for a 3D thumbnail image, a left image thumbnail and a right image thumbnail can be generated from a left image and a right image of an original image frame, respectively, and then combined to generate a single 3D thumbnail image. In general, the term "thumbnail" may be used to refer to a reduced image or a reduced still image. A generated left image thumbnail and right image thumbnail may be displayed with a horizontal distance difference there between by a depth corresponding to the disparity between the left image and the right image on the screen, thereby providing a stereoscopic space sense.

A left image and a right image required for implementing a 3D stereoscopic image may be displayed on the stereoscopic display unit using a stereoscopic processing unit. The stereoscopic processing unit can receive the 3D image and extract the left image and the right image, or can receive the 2D image and change it into a left image and a right image.

The audio output unit 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output unit 152 can provide audible output related to a particular function (e.g., a call signal reception sound, a message reception sound, etc.) performed by the HMD 100. The audio output unit 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the HMD 100.

An optical output unit 154 can output a signal for indicating an event generation using light of a light source. Examples of events generated in the HMD 100 may include message reception, call signal reception, a missed call, an alarm, a schedule notice, an email reception, information reception through an application, and the like. That is, the optical output unit 154 may serve to notify that the HMD 100 is performing a specific operation (function) by the user.

The signal output by the optical output unit 154 is implemented when the HMD emits light of a single color or a plurality of colors to the front or rear surface. The signal output may be terminated when the HMD detects the user's event confirmation or when the operation being performed on the HMD is finished.

The identification module may be a chip that stores various information for authenticating authority of using the HMD 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the HMD 100 via the interface unit 160.

When the HMD 100 is connected with an external cradle, the interface unit 160 can serve as a passage to allow power from the cradle to be supplied to the HMD 100 or may serve as a passage to allow various command signals input by the user from the cradle to be transferred to the HMD there through. Various command signals or power input from the cradle may operate as signals for recognizing that the HMD is properly mounted on the cradle.

The memory 170 can store programs to support operations of the controller 180 and store input/output data (for example, phonebook, messages, still images, videos, etc.). The memory 170 may store data associated with various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The HMD 100 may also be operated in relation to a network storage device that performs the storage function of the memory 170 over a network, such as the Internet.

The controller 180 can typically control the general operations of the HMD 100. For example, the controller 180 can set or release a lock state for restricting a user from inputting a control command with respect to applications when a status of the HMD meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provides internal power and supply the appropriate power required for operating respective elements and components included in the HMD 100. The power supply unit 190 may include a battery, which is typically rechargeable or be detachably coupled to the HMD for charging.

The power supply unit 190 may include a connection port. The connection port may be configured as one example of the interface unit 160 to which an external charger for supplying power to recharge the battery is electrically connected. As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance. Also, in the present disclosure, the term "memory 170" may also be referred to as the "storage unit 170".

The HMD device 100 can display an image. Specifically, the HMD device 100 can receive an image provided from an external device and display the received image. The image may be a virtual reality (VR) image.

The sensing unit 124 can acquire data about the movement of the HMD device 100. Specifically, the sensing unit 124 can acquire data about at least one of a moving direction, a movement amount, a rotating direction, and a rotation amount of the HMD device 100.

In order for the above-described operation, the sensing unit 124 may include a plurality of sensors. For example, the sensing unit 124 may include at least one of a gravity sensor, a geomagnetic sensor, a motion sensor, a gyro sensor, an acceleration sensor, an infrared sensor, an inclination sensor, a brightness sensor, an altitude sensor, an olfactory sensor, a temperature sensor, a depth sensor, a pressure sensor, a bending sensor, a bending sensor, an audio sensor, a video sensor, a Global Positioning System (GPS) sensor, and a touch sensor.

In addition, the communication unit 110 may be connected to a network in a wire or wireless manner to transmit and receive digital data such as content. The controller 180 can also control the display unit 151 to display an image. Specifically, when an image is received from an external device or when an image is stored in the storage unit 170, the controller 180 can control the display unit 151 to display the image.

Additionally, the controller 180 can acquire information about at least one of a moving direction, a movement amount, a rotating direction, and a rotation amount of the HMD device 100, based on the data about the movement of the HMD device 100 sensed by the sensing unit 124. Further, control information of the HMD device 100, which is acquired by the HMD device 100, can be transmitted to an external device. In this instance, the external device can provide an image corresponding to the control information of the HMD device 100 to the HMD device 100.

For example, when the control information of the HMD device 100 is information about the direction of the HMD device 100, the external device can provide an image corresponding to the direction of the HMD device 100 to the HMD device 100. In addition, various embodiments may be implemented within a recording medium readable by a computer or a similar device by using software, hardware, or combination thereof.

Figure 2:
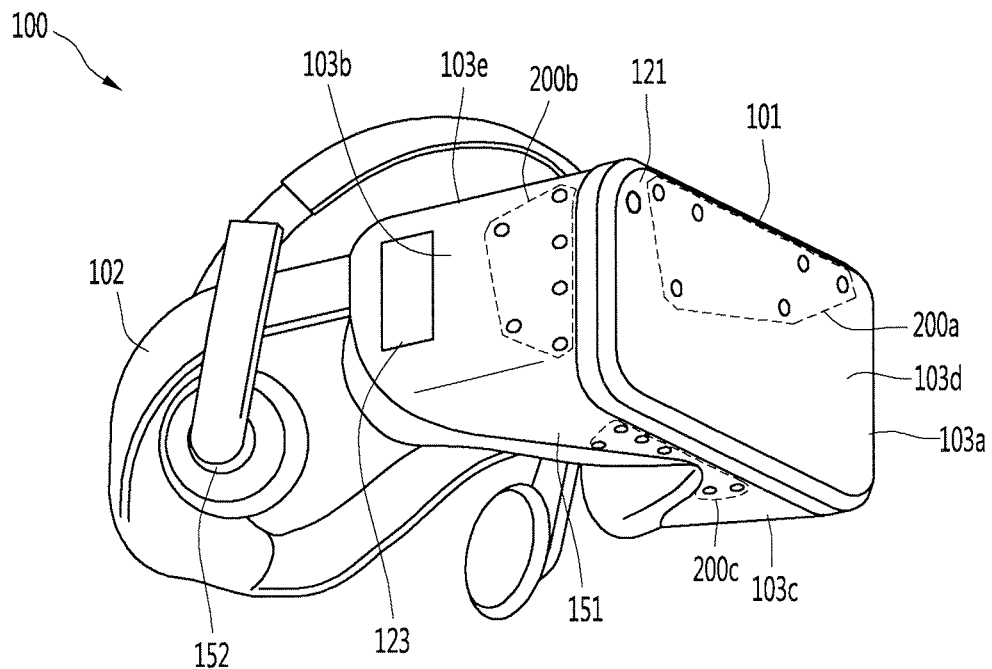
FIG. 2 is a conceptual diagram of the HMD related to the present disclosure, when viewed from one direction.

Next, FIG. 2 is a conceptual diagram of the HMD related to the present disclosure, when viewed from one direction. Referring to FIG. 2, the HMD 100 is formed to be wearable on a head (or a face) of a human body. Thus, the HMD 100 includes a frame part (case, housing, cover, etc.). The frame part may be made of a flexible material so as to facilitate wearing. FIG. 2 shows an example in which the frame part includes a first frame 101 and a second frame 102, which are made of different materials.

As an example, the first frame 101 provides a space in which at least one of the components described with reference to FIG. 1 can be disposed, and the second frame 102 can support (or fix) the first frame 101 so that the first frame 101 can be mounted on the head of the human body. The frame part may also be referred to as a main body (or HMD main body) or a body (or HMD body). The HMD main body (or HMD body) may be understood as a concept of referring to the HMD 100 as at least one aggregate.

The frame part is supported to the head and provides a space in which various parts are mounted. As shown in FIG. 2, a camera 121, electronic parts such as the output unit, the user input unit 123, the light-emitting units 200a, 200b, and 200c, the controller, and the sensing unit may be mounted on the first frame 101. The display unit 151 can cover at least one of the left eye and the right eye of the user (or to face at least one of the left eye and the right eye of the user) and be detachably formed.

Electronic parts such as the audio output unit 152 and the light-emitting units may be mounted on the second frame 102. However, the present disclosure is not limited thereto. The components described with reference to FIG. 1 and the components required for the HMD may be variously disposed on the first frame 101 and the second frame 102 by a user's selection. The controller 180 of FIG. 1 can control various electronic parts provided in the HMD 100.

The display unit 151 is mounted on the frame part and serves to output screen information (e.g., image, video, etc.) in front of the user's eyes. The display unit 151 may be disposed corresponding to at least one of the left eye and the right eye so that the screen information is displayed in front of the user's eye when the user wears the HMD 100. FIG. 2 shows an example in which the display unit 151 is disposed to cover both the left eye and the right eye of the user so that the image is displayed toward both the left eye and the right eye of the user.

Additionally, the display unit 151 can use a prism to project an image to the user's eyes. Additionally, the prism may be formed to be transmissive so that the user views the projected image and a general field of vision of the front (a range the user views through eyes) together.

As such, the image output through the display unit 151 can be viewed while overlapping with the general field of vision. The HMD 100 can use such characteristics of the display to provide augmented reality (AR) in which a virtual image is superimposed on a real image or a background and displayed as a single image.

Further, the camera 121 is disposed adjacent to at least one of the left eye and the right eye and configured to capture a front image. Since the camera 121 is disposed adjacent to the eyes to face the front, the camera 121 can acquire a scene the user views as an image. An example in which one camera 121 is provided is shown in FIG. 2, but the present disclosure is not necessarily limited thereto. A plurality of cameras 121 may be provided to acquire a three-dimensional (3D) image.

The HMD 100 may include the user input unit 123 which is manipulated so as to receive a control command. The user input unit 123 may be employed in any manner as long as the user operates in a tactile manner such as touch or push. An example in which the user input unit 123 using a push and touch input method is provided in the frame part is shown in FIG. 2.

Additionally, the HMD 100 may include a microphone which receives a sound and converts the sound into electrical audio data, and an audio output unit 152 which outputs the sound. The audio output unit 152 may be configured to transmit the sound in a general audio output method or a bond conduction method. When the audio output unit 152 is implemented in the bone conduction method, the audio output unit 152 is brought into close contact with the head when the user wears the HMD 100 and vibrates the skull to transmit the sound.

When the frame part including the first frame 101 and the second frame 102 is regarded as one HMD main body (hereinafter, referred to as a main body), the main body of the HMD related to the present disclosure may be formed in various shapes. Specifically, the main body may include a plurality of surfaces 103a, 103b, and 103c forming preset angles. The plurality of surfaces can be surfaces disposed at the outside of the main body. From this viewpoint, the plurality of surfaces may be the surfaces (outer surface or the like) of the HMD 100. The plurality of surfaces 103a, 103b, and 103c can be flat or curved.

Further, the display unit 151 of the HMD 100 related to the present disclosure can be disposed inside the main body. Specifically, the display unit 151 can be disposed inside the HMD 100, and be disposed at a position facing the user's eyes when the user wears the HMD 100 on the user's head.

The main body in which the plurality of surfaces 103a, 103b, and 103c are formed to be perpendicular to one another is shown in FIG. 2. Hereinafter, for convenience of explanation, the HMD in which the plurality of surfaces are formed to be perpendicular to one another will be described as an example, but the contents described in this connection can be applied to all types of HMDs including a plurality of surfaces forming preset angles in the same or similar manner.

Additionally, the second frame 102 of the HMD 100 may include a plurality of surfaces. In the present disclosure, any one surface 103f of the surfaces included in the second frame 102 is included in the plurality of surfaces of the HMD main body. The surface 103f can be disposed at the back of the head.

For example, referring to FIG. 2, the HMD according to the present disclosure may include a plurality of surfaces. The plurality of surfaces may include a front surface 103a, a left surface 103b, a lower surface 103c, a right surface 103d, an upper surface 103e, and a rear surface 103f.

The HMD 100 related to the present disclosure can also include a plurality of light-emitting units each formed on the plurality of surfaces of the main body and configured to emit light to the outside of the main body. Specifically, the plurality of light-emitting units may be respectively formed on the plurality of surfaces of the main body and emit light to the outside of the main body. Here, that the plurality of light-emitting units are respectively formed on the plurality of surfaces of the main body does not mean that a plurality of light-emitting units are formed for each of the plurality of surfaces, but means that one light-emitting unit is formed for each of the plurality of surfaces.

For example, as shown in FIG. 2, the first light-emitting unit 200a may be provided on the front surface 103a, the second light-emitting unit 200b may be provided on the left surface 103b, and the third light-emitting unit 200c may be provided on the lower surface 103c. In addition, the light-emitting units may be respectively provided on the right surface 103d, the upper surface 103e, and the rear surface 103f.

The plurality of light-emitting units may be used to determine (or estimate, track, detect, extract, decide, identify, recognize, etc.) the posture of the HMD 100. For example, in the present disclosure, the controller may be included for determine the posture of the HMD 100, and the controller 180 can determine the posture of the HMD 100 by using the plurality of light-emitting units respectively formed on the plurality of surfaces of the HMD 100.

The posture of the HMD 100 may be understood as a concept including when the HMD 100 is placed (when the HMD 100 is worn on the head of the user), a degree of inclination of the HMD 100, a direction the HMD 100 faces, a position of the HMD 100, a rotation of the HMD 100, a movement of the HMD 100, and the like. Additionally, in the present disclosure, that the posture of the HMD 100 is determined means that the posture and movement of the user wearing the HMD 100 is determined.

The plurality of light-emitting unit may include a plurality of light-emitting devices. Each light-emitting unit may be formed so that the plurality of light-emitting devices have different patterns (arrangements) so as to distinguish the plurality of surfaces from one another.

For example, the pattern (or arrangement) in which the plurality of light-emitting devices included in the light-emitting unit 200*a* provided on the front surface 103*a* are arranged may be different from the pattern in which the plurality of light-emitting devices included in the light-emitting unit provided on the surface different from the front surface (for example, the light-emitting unit 200*b* provided on the left surface 103*b*).

The controller may identify the light-emitting unit based on the plurality of light-emitting devices arranged on the plurality of surfaces to have different patterns, and can determine the posture of the HMD 100 by using the identified light-emitting unit. Also, the term "HMD 100" may also be referred to as the "HMD device 100".

Figure 3:
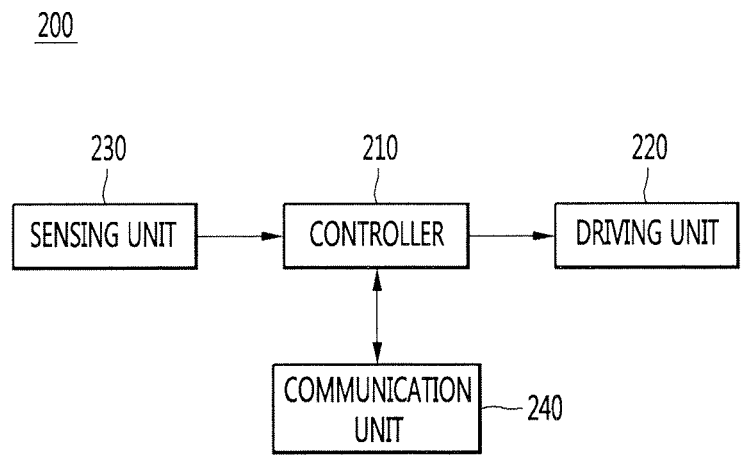
FIG. 3 is a block diagram illustrating a massage chair according to an embodiment of the present disclosure.

Next, FIG. 3 is a block diagram illustrating a massage chair 200 according to an embodiment of the present disclosure. The massage chair 200 may include at least one of a controller 210, a driving unit 220, a sensing unit 230, and a communication unit 240.

Further, the controller 210 performs an overall control of each component of the massage chair 200. Specifically, the controller 210 can control the operations of the driving unit 220, the sensing unit 230, and the communication unit 240.

Figure 4:
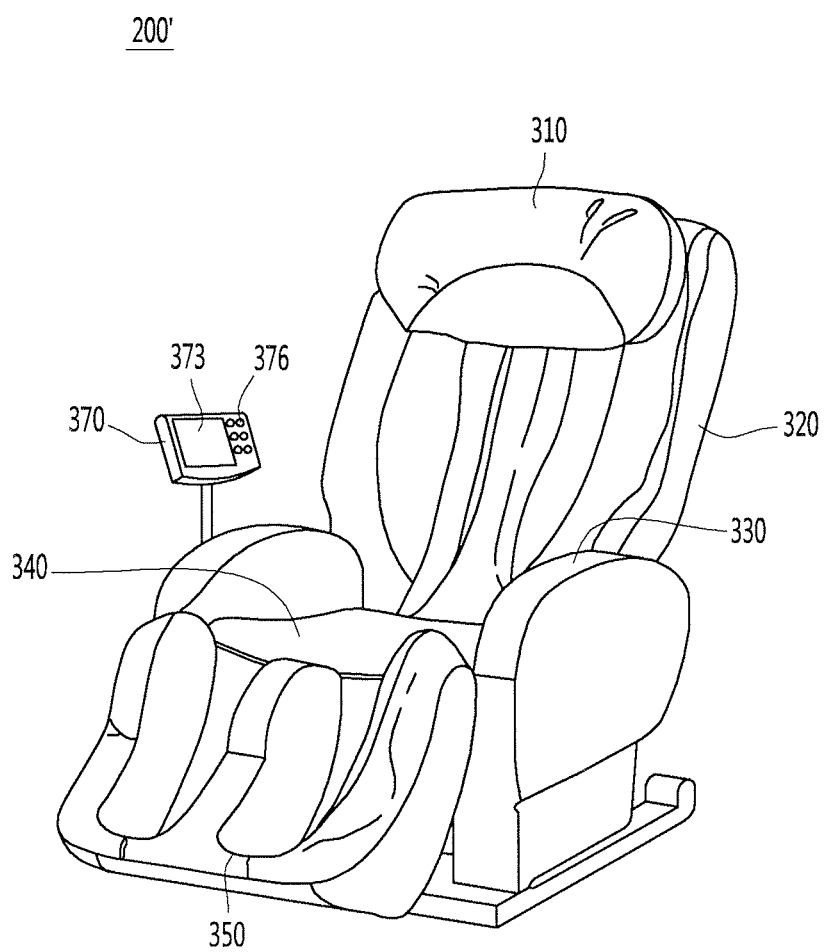
FIG. 4 is a perspective view illustrating a structure of a massage chair according to an embodiment of the present disclosure.

The driving unit 220 can generate a force for performing massage under the control of the controller 210. Further, the driving unit 220 can transmit the generated force to at least one of a head massage unit 310 supporting the user's head, a back massage unit 320 supporting the user's back, an arm massage unit 330 supporting the user's arm, a hip massage unit 340 supporting the user's hip, and a leg massage unit 350 supporting the user's leg (FIG. 4).

In addition, the driving unit 220 can generate a force for rotating at least one of the head massage unit 310 supporting the user's head, the back massage unit 320 supporting the user's back, the arm massage unit 330 supporting the user's arm, the hip massage unit 340 supporting the user's hip, and the leg massage unit 350 supporting the user's leg and transmit the generated force thereto.

Thus, the driving unit 220 may include at least one motor configured to generate a rotating force, and a power transmission unit configured to transmit the generated rotating force.

Each of the head massage unit 310, the back massage unit 320, the arm massage unit 330, the hip massage unit 340, and the leg massage unit 350 may include an airbag, and the driving unit 220 can perform a massage with various strengths by adjusting air pressure of the airbag of each of the massage unit 310, the back massage unit 320, the arm massage unit 330, the hip massage unit 340, and the leg massage unit 350.

The sensing unit 230 can acquire data for acquiring information about at least one of a body shape, a posture, and a position of the user. Specifically, the sensing unit 230 may include at least one sensor disposed at a portion that the user contacts. The at least one sensor may include at least one of an electrostatic sensor, a pressure sensor, and a piezoelectric sensor. When the user contacts the massage chair, the at least one sensor can acquire data about at least one of a contact surface and a contact strength.

In this instance, the controller 210 can acquire information about at least one of the body shape, the posture, and the position of the user, based on the data acquired by the sensing unit 230. Further, the sensor included in the sensing unit 230 is not limited to the electrostatic sensor, the pressure sensor, and the piezoelectric sensor described above, and may be any sensors capable of collecting data for acquiring the information about at least one of the body shape, the posture, and the position of the user. Examples of such sensors may include an ultrasonic sensor, an optical sensor, and the like.

Also, the sensing unit 230 can acquire data for acquiring information about a slope of the massage chair. The information about the slope of the massage chair may include at least one of slope information of the head massage unit, slope information of the back massage unit, slope information of the hip massage unit, slope information of the leg massage unit, slope information of the arm massage unit, and slope information of the entire massage chair.

Specifically, the massage chair may include at least one of the head massage unit, the back massage unit, the hip massage unit, the arm massage unit, and the leg massage unit. The sensing unit 230 may include at least one sensor capable of sensing the rotation of at least one of the head massage unit, the back massage unit, the hip massage unit, the arm massage unit, and the leg massage unit. Additionally, the entire massage chair may be rotated, and the sensing unit 230 may measure the rotation or the slope of the massage chair. The at least one sensor included in the sensing unit 230 may be at least one of an inertial sensor, a magnetic sensor, a gravity sensor, a gyroscope sensor, and an acceleration sensor.

In addition, the controller 210 can acquire information about the slope of the massage chair, based on the data acquired by the sensing unit 230. Also, the communication unit 240 can communicate with the HMD 100. Specifically, the communication unit 240 may be connected to the HMD 100 in a wired or wireless manner to transmit data to the HMD 100 or receive data from the HMD 100.

Next, FIG. 4 is a perspective view illustrating the structure of the massage chair 200 according to an embodiment of the present disclosure. The massage chair 200 may include at least one of the head massage unit 310 supporting the user's head, the back massage unit 320 supporting the user's back, the arm massage unit 330 supporting the user's arm, the hip massage unit 340 supporting the user's hip, and the leg massage unit 350 supporting the user's leg.

At least one of the head massage unit 310, the back massage unit 320, the arm massage unit 330, the hip massage unit 340, and the leg massage unit 350 can be vertically rotated by the force transmitted from the driving unit 220. Each of the head massage unit 310, the back massage unit 320, the arm massage unit 330, the hip massage unit 340, and the leg massage unit 350 may include at least one roller or at least one massage rod and can perform massage through a preset operation by the force transmitted from the driving unit 220.

Each of the head massage unit 310, the back massage unit 320, the arm massage unit 330, the hip massage unit 340, and the leg massage unit 350 may include an airbag. Massage of various strengths can be provided to the user by adjusting the air pressure of the airbag included in each of the head massage unit 310, the back massage unit 320, the arm massage unit 330, the hip massage unit 340, and the leg massage unit 350.

Further, the massage chair 200 may include a support which constitutes a framework inside the massage chair 200. The entire massage chair 200 may be horizontally or vertically rotated by the force transmitted from the driving unit 220. Also, the massage chair 200 may include a user interface unit 370 having a display unit 373 configured to display information under the control of the controller 210, and an input unit 376 configured to receive an input from the user and transmit the input to the controller 210.

Each of the head massage unit 310, the back massage unit 320, the arm massage unit 330, the hip massage unit 340, and the leg massage unit 350 may include at least one lower massager. For example, the head massage unit 310 may include at least one of a head massager capable of massaging the user's head and a neck massager capable of massaging the user's neck. As another example, the back massage unit 320 may include at least one of a shoulder massager capable of massaging the user's shoulder, a back massager capable of massaging the user's back, and a waist massager capable of massaging the user's waist. As another example, the leg massage unit 350 may include at least one of a thigh massager capable of massaging the user's thigh, a calf massager capable of massaging the user's calf, and a foot massager capable of massaging the user's foot.

The structure and the operating method of the massage chair 200 have been described above, but the present disclosure is not limited to the above-described massage chair 200. Specifically, the structure and the operating method of the massage chair are disclosed in various documents, and the massage chair 200 according to the embodiment of the present disclosure may be applied to various types of known massage chairs.

Figure 5:
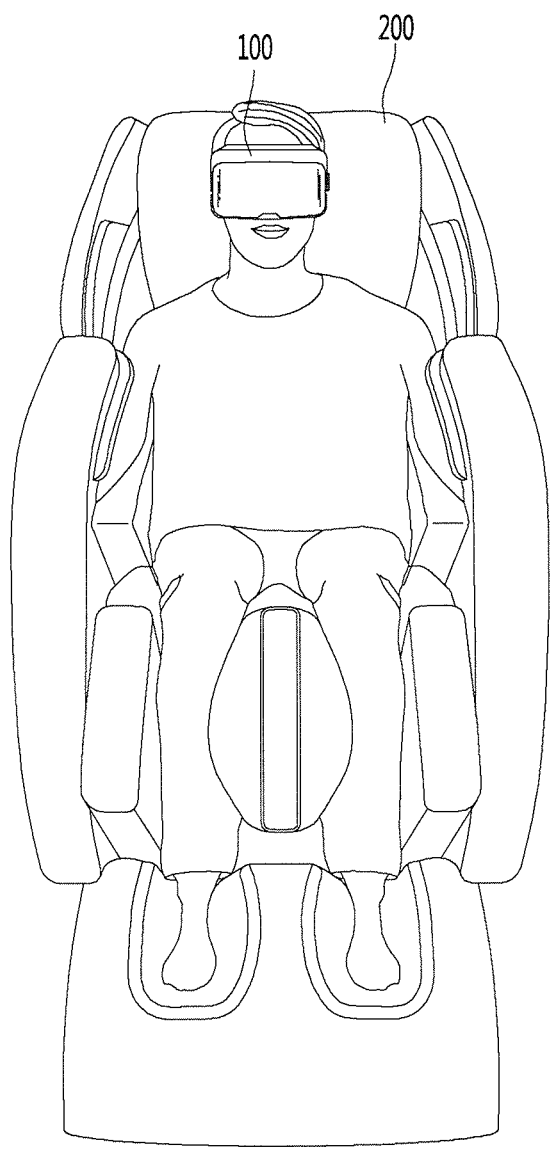
FIG. 5 is a view illustrating a situation in which a user wearing an HMD receives a massage on a massage chair, according to an embodiment of the present disclosure.

Next, FIG. 5 is a view illustrating a situation in which the user wearing the HMD receives a massage on the massage chair, according to the embodiment of the present disclosure. Also, the communication unit 110 of the HMD 100 can be connected to the communication unit 240 of the massage chair 200 to transmit and receive data.

Specifically, the controller 180 of the HMD 100 can transmit the control command to the massage chair 200 through the communication unit 110. The control command may include at least one of a massage mode control command, a massage strength control command, a massage part control command, a massage speed control command, and a massage pattern control command.

When the control command is received from the HMD 100, the controller 210 of the massage chair 200 can perform the operation corresponding to the control command. Specifically, the controller 210 of the massage chair 200 may adjust at least one of a massage mode, a massage strength, and a massage speed, based on the received control command.

Further, the controller 210 of the massage chair 200 can transmit massage information to the HMD 100 through the communication unit 240. The massage information may include at least one of information about the slope of the massage chair 200, information about the massage part, information about the massage mode, and information about the massage pattern.

When the massage information is received from the massage chair 200, the controller 180 of the HMD 100 can control the operation of the HMD 100 based on the received massage information or can transmit the control command to the massage chair 200.

Figure 6:
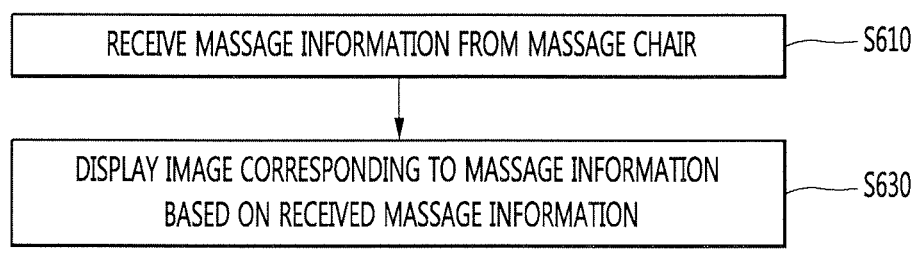
FIG. 6 is a flowchart illustrating an operating method of an HMD device according to an embodiment of the present disclosure.

Next, FIG. 6 is a flowchart illustrating an operating method of the HMD device according to an embodiment of the present disclosure. As shown, the operating method of the HMD device includes receiving massage information from the massage chair (S610), and displaying an image corresponding to the massage information based on the massage information (S630).

Figure 7:
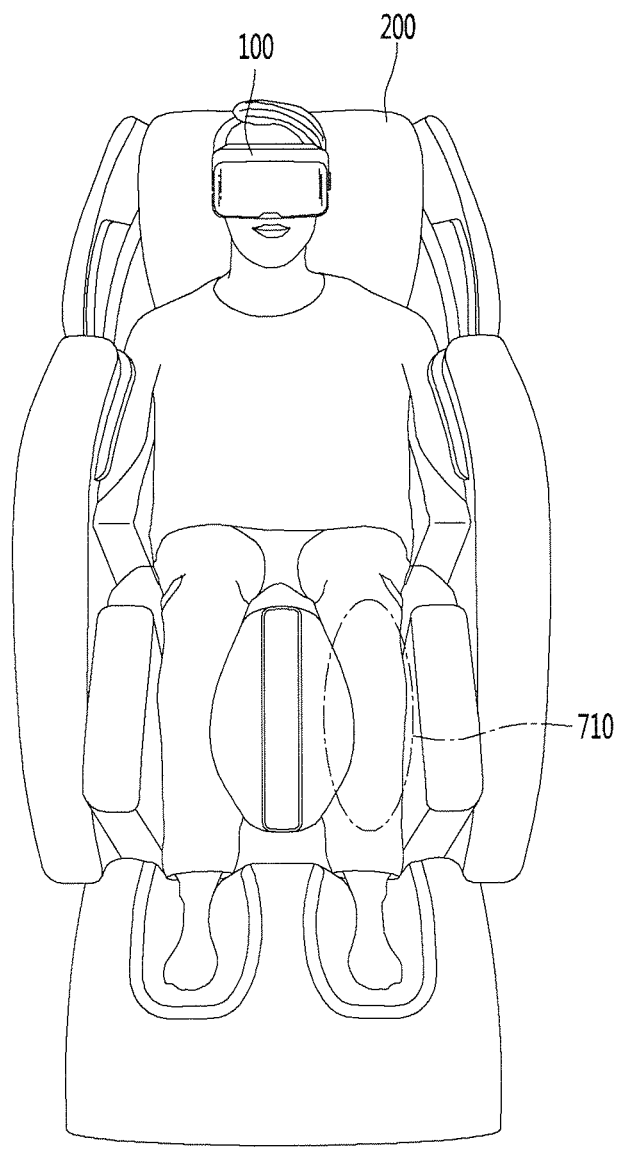
FIG. 7 is a view illustrating a method of receiving massage information from a massage chair according to an embodiment of the present disclosure.

FIG. 7 is a view illustrating the method of receiving the massage information from the massage chair according to an embodiment of the present disclosure. That is, the controller 180 of the HMD device can receive massage information from the massage chair 200, and the massage information may include information about the massage part of the user receiving the massage.

In more detail, the body of the user includes a plurality of massage parts including at least one of a user's head, neck, left shoulder, right shoulder, back, waist, hip, left arm, right arm, left thigh, right thigh, left calf, and right calf. However, the present disclosure is not limited thereto, and massage parts defined by integrating the plurality of massage parts may exist. For example, the plurality of massage parts may include at least one of a user's head, neck, shoulder, waist, hip, arm, and leg.

In addition, the controller 210 of the massage chair 200 can transmit information about the massage part being massaged to the HMD device 100. Specifically, when a first massage part 710 among the plurality of massage parts is being massaged, the controller 210 of the massage chair 200 can transmit, to the HMD device 100, information indicating that the first massage part 710 is being massaged. For example, when the left calf is being massaged, the controller 210 of the massage chair 200 can transmit, to the HMD device 100, information indicating that the left calf is being massaged.

In addition, the massage information may include information about the massage mode. In more detail, the massage mode may be at least one mode corresponding to at least one style. For example, when a first massage mode is a mode that performs a Thailand-style massage, a second massage mode may be a mode that performs a Chinese-style massage.

Figure 8:
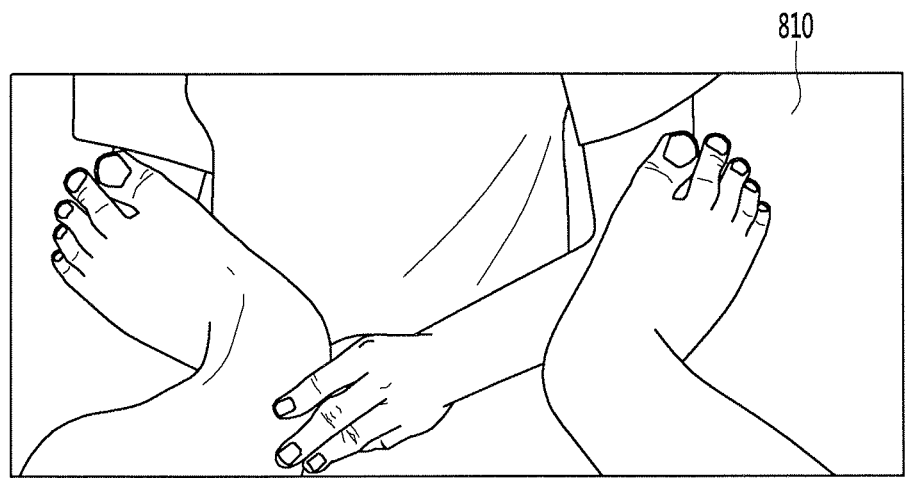
FIG. 8 is a view illustrating a method of displaying an image corresponding to massage information based on massage information according to an embodiment of the present disclosure.

Next, FIG. 8 is a view illustrating a method of displaying an image based on the received massage information according to an embodiment of the present disclosure. In addition, the controller 180 can display an image based on received massage information.

Specifically, the controller 180 can display an image in which the massage part is massaged, based on the received information about the massage part. For example, when the information indicating that the left calf is being currently massaged is received from the massage chair 200, the controller 180 can display an image 810 in which the left calf is massaged, as shown in FIG. 8.

In addition, the controller 180 can display an image in which the massage is performed in the massage mode of the massage chair 200, based on the information about the massage mode of the massage chair 200. Specifically, when the massage mode of the massage chair 200 is a first massage mode, the controller 180 can display an image showing characteristics of the first massage mode. When the massage mode of the massage chair 200 is a second massage mode, the controller 180 can display an image showing characteristics of the second massage mode.

For example, when the first massage mode is a mode that performs a Thailand-style massage characterized by loosening muscles by pressing knotted muscles with fingers, the controller 180 can display an image in which the body is pressed with fingers. Additionally, when the second massage mode is a mode that performs a Chinese-style massage characterized by softly rubbing the skin, the controller 180 can display an image in which the skin is softly rubbed.

As another example, when the first massage mode is a pressing mode, the controller 180 can display an image in which the body is pressed. Additionally, when the second massage mode is a beating or hard pressing mode, the controller 180 can display an image in which the body is beaten or pressed hard.

Also, the controller 180 can receive a user's health information from the massage chair 200. Specifically, the sensing unit 230 of the massage chair 200 can acquire data associated with the user's health. For example, the sensing unit 230 of the massage chair 200 may include at least one sensor capable of acquiring data associated with the user's health, such as muscle stiffness, blood pressure, pulse, body temperature, and body fat.

In addition, the controller 210 of the massage chair 200 can acquire the user's health information based on the data acquired by the sensing unit 230. The user's health information may include at least one of muscle stiffness, blood pressure, pulse, body temperature, and body fat. The controller 210 of the massage chair 200 can also transmit the health information to the HMD device 100.

Further, the controller 180 can display an image of recommending the massage mode corresponding to the user's health, based on the health information. Additionally, when an input of selecting the recommended massage mode is received, the controller 180 can transmit a command for operating as the recommended massage mode to the massage chair 200.

Also, the controller 180 can display a body image and display information indicating a health degree of the user together the body image, based on the user's health information. For example, the controller 180 can display a body image including a plurality of muscles and display information indicating stiffness of each muscle together the body image.

When the health degree is changed as the massage progresses, the controller 180 can display information indicating the changed health degree. For example, when a plurality of muscles are relaxed as the massage is progressed, the stiffness of each muscle can be lowered. In this instance, the controller 180 can display information indicating the changed stiffness of each muscle together the body image.

In addition, the controller 180 can display an image in which the first massage part having a low health degree among the plurality of massage parts is massaged. For example, when the left calf is most stiffened and thus has the greatest stiffness, the controller 180 can display an image in which the left calf having the greatest stiffness among the plurality of massage parts is massaged.

Further, the controller 180 can display information indicating the health degree of the first massage part together with the image in which the first massage part is massaged. For example, the controller 180 can display an image showing the stiffness of the left calf together with the image in which the first massage part is massaged.

When the health degree of the first massage part is changed as the massage progresses, the controller 180 can display information indicating the changed health degree of the first massage part. For example, when the muscle of the left calf is relaxed as the massage is progressed, the stiffness of the left calf may be lowered. In this instance, the controller 180 can display information indicating the changed stiffness of the left calf together the image in which the left calf is massaged.

An example of displaying the image corresponding to the massage mode of the massage chair, the massage part, or the user's health information has been described, but the present disclosure is not limited thereto. The massage mode of the massage chair, the massage part, or the user's health information may be combined. For example, the controller 180 can display an image in which a particular massage part is massaged in a particular massage mode, based on the information about the massage mode and the massage part. That is, when the left calf is massaged in the Thailand-style massage mode and characteristics of the Thailand-style massage mode are to loosen muscles by pressing muscles with fingers, the controller 180 can display an image in which the left calf is pressed with fingers.

Figure 9:
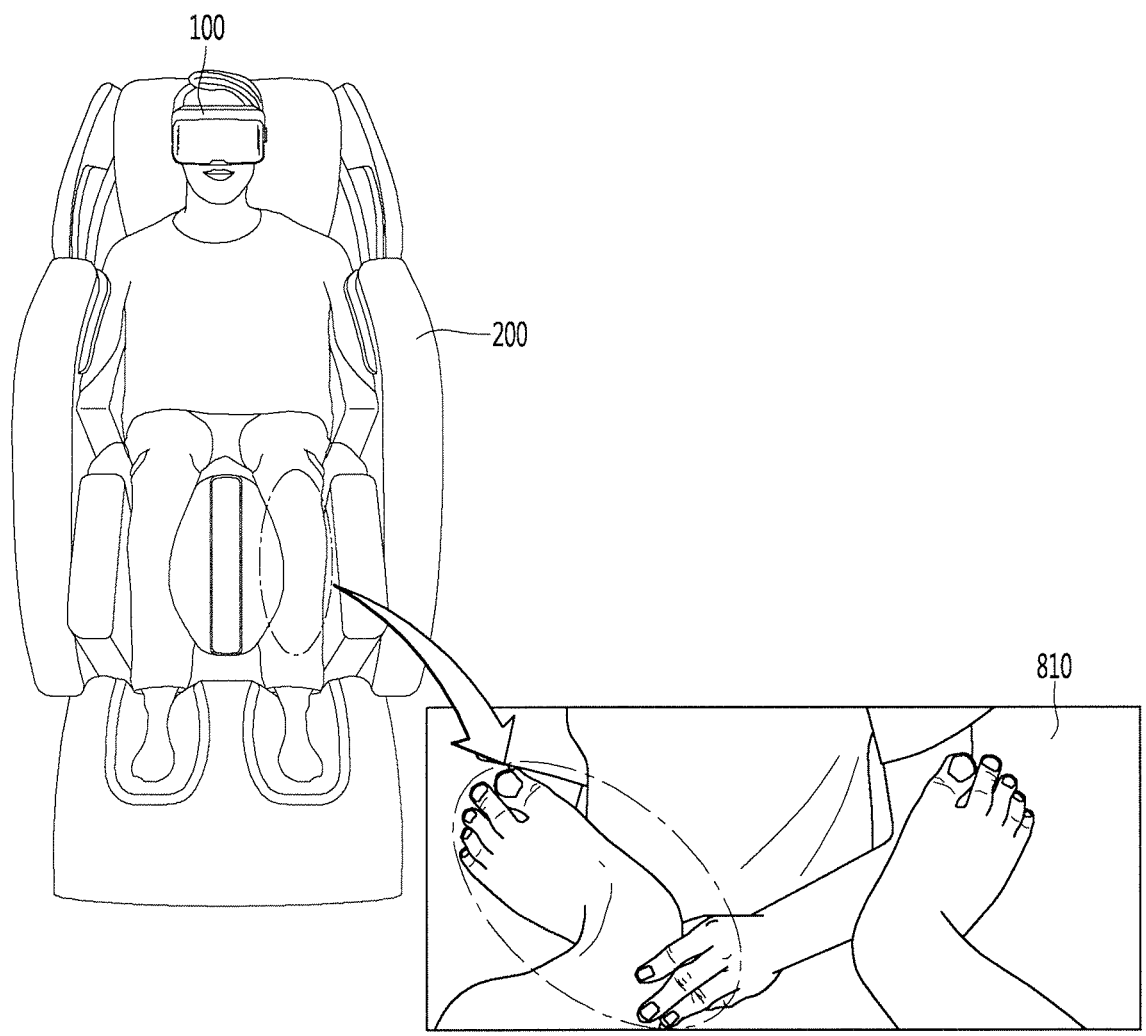
FIG. 9 is a view illustrating a method of synchronizing a real massage operation with an image based on synchronization information about press and release according to an embodiment of the present disclosure.

Next, FIG. 9 is a view illustrating a method of synchronizing a real massage operation with an image based on synchronization information about pressure and release according to an embodiment of the present disclosure. The massage chair 200 can perform massage on a particular massage part by repeating a press and release.

Further, the controller 210 of the massage chair 200 can transmit synchronization information about the press and release to the HMD device. The synchronization information may be a synchronization signal indicating at least one of the time when the press is applied to the particular massage part in the massage chair 200 and the time when the press of the particular massage part is released in the massage chair 200.

In addition controller 180 of the HMD device can receive massage information from the massage chair 200. The massage information may be synchronization information about the press and the release of the particular massage part. Based on the synchronization information about the press and the release, the controller 180 can display a first image when the massage chair presses at least one massage part, and display a second image when the press of at least one massage part is released.

Specifically, based on the information about the massage part being massaged and the synchronization information about the press and the release, the controller 180 can display an image in which the particular massage part is pressed, when the massage chair 200 presses the particular massage part, and display an image in which the press of the particular massage part is released, when the massage chair releases the press of the particular massage part. For example, when the massage chair 200 presses the left calf, the controller 180 can display an image in which the hand of the massager presses the left calf, and when the massage chair 200 releases the press of the left calf, the controller 210 may display an image in which the hand of the massager does not press the left calf.

Figure 10:
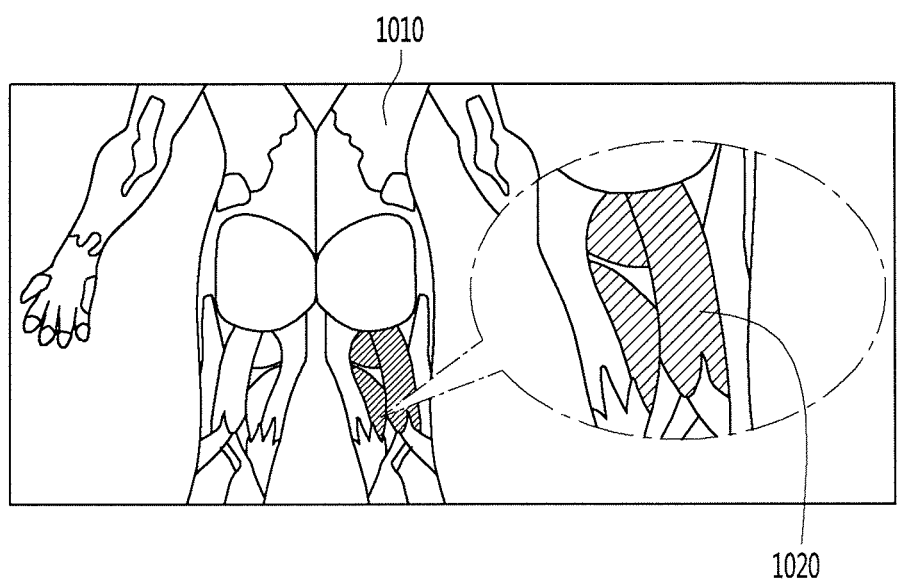
FIG. 10 is a view illustrating a method of displaying an image indicating that a muscle is relaxed, according to an embodiment of the present disclosure.

Next, FIG. 10 is a view illustrating a method of displaying an image indicating that a muscle is relaxed, according to an embodiment of the present disclosure. As shown, the controller 180 can display a body image 1010 showing that a plurality of muscles are relaxed.

Specifically, the body image 1010 may include a plurality of muscles in the body. Further, the controller 180 can display each muscle in a color corresponding to a degree of relax of each muscle. For example, a muscle can be displayed in a red color when the muscle is not relaxed at all, a muscle can be displayed in a yellow color when the muscle is being relaxed, and a muscle can be displayed in a blue color when the muscle is completely relaxed. The controller

180 can display a muscle around the neck in a red color, display a muscle around the left arm in a yellow color, and display a muscle around the hip in a blue color.

In addition, the controller 180 can display information about a muscle having a fastest massage progress status among the plurality of muscles. For example, when the relax status of the muscle around the hip among the plurality of muscles is fastest, the controller 180 can display an image 1020 showing the muscle around the hip.

Additionally, the controller 180 can display a muscle having a fastest massage progress status in a color corresponding to a degree of relax of the muscle. For example, the controller 180 can display the muscle around the hip in a blue color.

Figure 11:
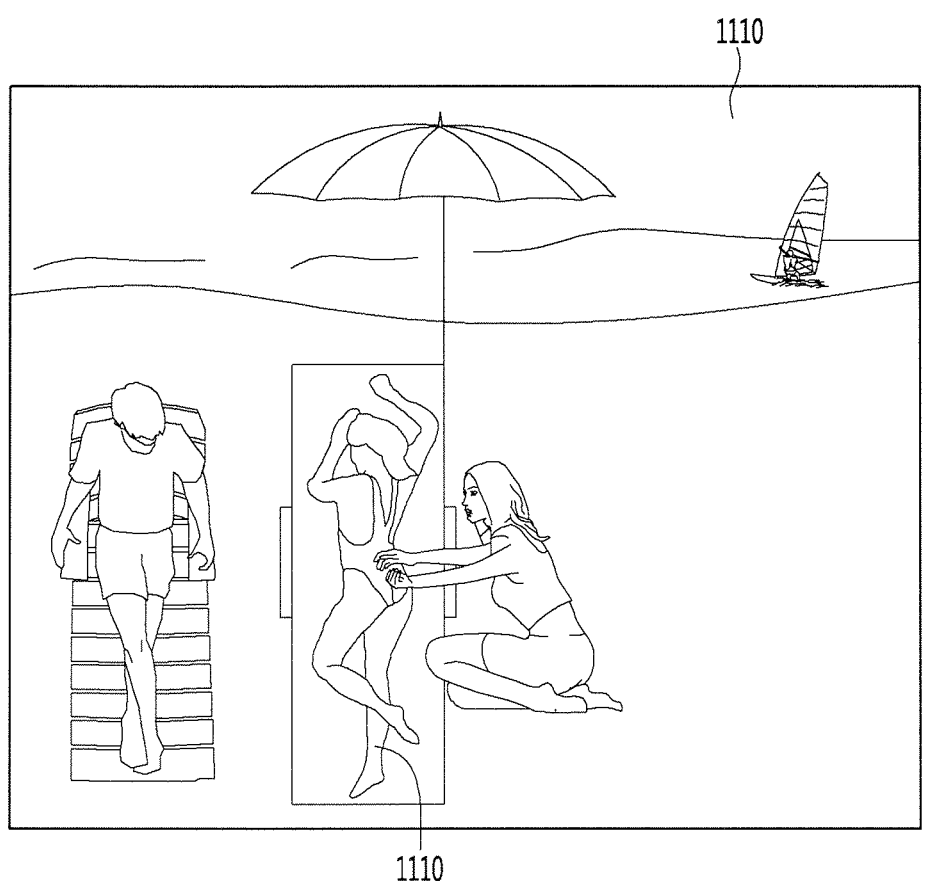
FIG. 11 is a view illustrating a method of displaying a changed background screen according to an embodiment of the present invention.

Next, FIG. 11 is a view illustrating a method of displaying a changed background screen according to an embodiment of the present disclosure.

The controller 180 can display a background screen 1120 together with an image 1110 corresponding to massage information. For example, the controller 180 can display a background screen showing a sea together with the image 1110 corresponding to the massage information. As another example, the controller 180 can display a background screen showing a desert or a background screen showing a red clay room together with the image 1110 corresponding to the massage information.

In this instance, the controller 180 can change the background screen 1120 and display the changed background screen 1120, based on a user input for changing the background screen. The controller 180 can display a background screen corresponding to a massage mode together with an image corresponding to massage information. For example, when the massage mode of the massage chair 200 is a mode that performs a Thailand-style massage, the controller 180 can display a background screen showing the Thailand together with the image corresponding to the massage information.

An image display system of the HMD device interworking with the massage chair will be described below. All the embodiments described above can be applied to the image display system of the HMD device interworking with the massage chair. The massage chair 200 can acquire massage information including at least one of information about the massage part, information about the massage mode, synchronization information about the press and the release, and user's health information, and transmit the acquired massage information to the HMD device. The HMD device 100 can receive the massage information and display an image corresponding to the massage information based on the received massage information.

The present invention mentioned in the foregoing description may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments are merely exemplary and are not to be considered as limiting the present disclosure. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A head mounted display (HMD) device comprising:
a display configured to display an image;
a communication processor configured to communicate with a massage chair for performing a massage; and
a controller configured to:
transmit a control command to the massage chair, wherein the control command includes at least one of a massage mode control command, a massage strength control command, a massage part control command, a massage speed control command, and a massage pattern control command,
receive massage information from the massage chair about the massage, wherein the received massage information includes information about a massage part of a user receiving the massage, information about a massage mode, synchronization information about a press and release of the massage, and muscle stiffness acquired based on at least one sensor disposed at a portion that the user contacts, wherein the at least one sensor includes at least one of an electrostatic sensor, a pressure sensor or a piezoelectric sensor,
display an image on the display corresponding to the massage based on the received massage information,
display the image including a body image showing a plurality of muscles of the user and a muscle among the plurality of muscles being massaged, based on the information about the massage part, and
determine a muscle relax degree based on the muscle stiffness, and display each of the plurality of muscles in a color corresponding to the muscle relax degree for each of the plurality of muscles,
wherein the synchronization information about the press and release of the massage is a synchronization signal indicating a time when the press is applied to a particular massage part in the massage chair and a time when the press of the particular massage part is released,
wherein the controller is configured to display the image in which a hand presses the particular massage part when the massage chair presses the particular massage part, based on the massage part of the user receiving the massage and the synchronization information about the press and release of the massage, and
wherein the controller is configured to display the image in which the particular massage part is pressed when the massage mode of the massage chair is a pressing mode, display the image in which the particular massage part is beaten when the massage mode of the massage chair is a beating mode, based on the information about the massage mode.

2. The HMD device according to claim 1, wherein the received massage information further includes health information of the user.

3. The HMD device according to claim 2, wherein the displayed image illustrates a type of the massage mode, based on the information about the massage mode.

4. The HMD device according to claim 2, wherein the health information is acquired based on data associated with the user's health collected by at the least one sensor and includes at least one the muscle stiffness, blood pressure, pulse, body temperature and body fat, and
wherein the controller is further configured to:
display information on the display indicating a health degree of the user together with the body image based on the health information, and
display changed health degree information indicating a changed health degree when the health degree is changed as the massage progresses.

5. The HMD device according to claim 4, wherein the controller is further configured to:
display the health information further indicating a health degree of the muscle being massaged among the plurality of muscles with the displayed body image, and
display the changed health degree information indicating the changed health degree of the muscle being massage when the health degree of the muscle being massaged among the plurality of muscles is changed as the massage progresses.

6. The HMD device according to claim 2, wherein the controller is further configured to display a background screen corresponding to the massage mode together with the image corresponding to the massage.

7. An image display system comprising:
a massage chair configured to perform a massage; and
a head mounted display (HMD) configured to:
transmit a control command to the massage chair, wherein the control command includes at least one of a massage mode control command, a massage strength control command, a massage part control command, a massage speed control command, and a massage pattern control command,
receive massage information from the massage chair about the massage, wherein the received massage information includes information about a massage part of a user receiving the massage, information about a massage mode, synchronization information about a press and release of the massage, and muscle stiffness acquired based on at least one sensor disposed at a portion that the user contacts, wherein the at least one sensor includes at least one of an electrostatic sensor, a pressure sensor or a piezoelectric sensor, and
display an image on a display of the HMD corresponding to the massage based on the received massage information,
wherein the HMD is configured to display the image including a body image showing a plurality of muscles of the user and a muscle among the plurality of muscles being massaged, based on the information about the massage part,
wherein the HMD is configured to determine a muscle relax degree based on the muscle stiffness, and display each of the plurality of muscles in a color corresponding to the muscle relax degree for each of the plurality of muscles,
wherein the synchronization information about the press and release of the massage is a synchronization signal indicating a time when the press is applied to a particular massage part in the massage chair and a time when the press of the particular massage part is released,
wherein the HMD is configured to display the image in which a hand presses the particular massage part when the massage chair presses the particular massage part, based on the massage part of the user receiving the massage and the synchronization information about the press and release of the massage, and
wherein the HMD is configured to display the image in which the particular massage part is pressed when the massage mode of the massage chair is a pressing mode, display the image in which the particular massage part is beaten when the massage mode of the massage chair is a beating mode, based on the information about the massage mode.

8. The image display system according to claim 7, wherein the received massage information further includes health information of the user.

9. The image display system according to claim 8, wherein the displayed image illustrates a type of the massage mode, based on the information about the massage mode.

10. The image display system according to claim 8, wherein the health information is acquired based on data associated with the user's health collected by the at least one sensor and includes at least one the muscle stiffness, blood pressure, pulse, body temperature and body fat, and
wherein the HMD device:
displays the health information indicating a health degree of the muscle being massaged among the plurality of muscles together with the displayed body image, and
displays a changed health degree information indicating the changed health degree of the muscle being massaged among the plurality of muscles when the health degree of the muscle being massaged among the plurality of muscles is changed as the massage progresses.

* * * * *